United States Patent
Mitra (10) Patent No.: US 6,765,038 B2
(45) Date of Patent: Jul. 20, 2004

(54) GLASS IONOMER CEMENT

(75) Inventor: Sumita B. Mitra, West Saint Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 404 days.

(21) Appl. No.: 09/916,399

(22) Filed: Jul. 27, 2001

(65) Prior Publication Data

US 2003/0087986 A1 May 8, 2003

(51) Int. Cl.⁷ .......................... A61K 6/083; A61C 5/00; C08K 3/34
(52) U.S. Cl. ...................... 523/115; 523/116; 523/118; 523/120; 524/443; 526/227; 433/228.1
(58) Field of Search ................................ 523/115, 116, 523/118, 120; 524/443; 526/227; 433/228.1

(56) References Cited

U.S. PATENT DOCUMENTS

| | | |
|---|---|---|
| 4,070,199 A | 1/1978 | Downing et al. |
| 4,209,434 A | 6/1980 | Wilson et al. |
| 4,317,681 A | 3/1982 | Beede et al. |
| 4,337,186 A | 6/1982 | Crisp et al. |
| 4,374,936 A | 2/1983 | Tomioka et al. |
| 4,376,835 A | 3/1983 | Schmitt et al. |
| 4,652,593 A | 3/1987 | Kawahara et al. |
| 4,758,612 A | 7/1988 | Wilson et al. |
| 4,808,228 A | 2/1989 | Randklev |
| 4,871,531 A | 10/1989 | Hartlaub et al. |
| 4,872,936 A | 10/1989 | Engelbrecht |
| 4,900,697 A | 2/1990 | Akahane et al. |
| 5,063,257 A | 11/1991 | Akahane et al. |
| 5,130,347 A | 7/1992 | Mitra |
| 5,154,762 A | 10/1992 | Mitra et al. |
| 5,227,413 A | 7/1993 | Mitra |
| 5,318,999 A | 6/1994 | Mitra et al. |
| 5,332,429 A | 7/1994 | Mitra et al. |
| 5,367,002 A | 11/1994 | Huang et al. |
| 5,378,785 A | 1/1995 | Mitra |
| 5,382,284 A | 1/1995 | Arnold |
| 5,453,456 A | 9/1995 | Mitra et al. |
| 5,501,727 A | 3/1996 | Wang et al. |
| 5,512,611 A | 4/1996 | Mitra |
| 5,520,725 A | 5/1996 | Kato et al. |
| 5,520,922 A | 5/1996 | Gasser et al. |
| 5,552,485 A | 9/1996 | Mitra et al. |
| 5,670,258 A | 9/1997 | Mitra et al. |
| 5,814,682 A | 9/1998 | Rusin et al. |
| 5,844,019 A | 12/1998 | Kato |
| 5,859,089 A | 1/1999 | Qian |
| 5,871,360 A | 2/1999 | Kato |
| 5,922,786 A * | 7/1999 | Mitra et al. .................. 523/118 |
| 5,925,715 A | 7/1999 | Mitra |
| 5,962,550 A | 10/1999 | Akahane et al. |
| 5,965,632 A | 10/1999 | Orlowski et al. |
| 6,126,922 A | 10/2000 | Rozzi et al. |
| 6,217,644 B1 | 4/2001 | Matsunae et al. |

FOREIGN PATENT DOCUMENTS

| | | |
|---|---|---|
| EP | 0 329 268 A2 | 8/1989 |
| EP | 0 430 705 B1 | 10/1993 |
| EP | 0 323 120 B1 | 3/1994 |
| EP | 0 923 925 A2 | 6/1999 |
| WO | WO 92/21632 | 12/1992 |
| WO | WO 94/23687 | 10/1994 |
| WO | WO 97/18792 | 5/1997 |
| WO | WO 97/47272 | 12/1997 |

OTHER PUBLICATIONS

U.S. patent application Ser. No. 09/753,945, filed Jan. 3, 2001.

R.S. Mathis and J.L. Ferracane, "Properties of a New Glass Ionomer/Composite Resin Hybrid Restorative," Baylor College of Dentistry, Dallas, Texas (Abstract #51)(1987).

* cited by examiner

*Primary Examiner*—Tae H. Yoon
(74) *Attorney, Agent, or Firm*—Sean J. Edman (57) ABSTRACT

Resin-modified glass ionomer cements contain a polymer having a plurality of acidic repeating units but being substantially free of polymerizable vinyl groups, a polymer having a plurality of acidic repeating units and a plurality of polymerizable vinyl groups, a fluoroaluminosilicate glass, a redox cure system that can initiate dark cure of the vinyl groups, and water. The cements can be used without requiring a preliminary tooth priming or conditioning step and without requiring a curing lamp. The cements offer ease of mixing, convenient viscosity, convenient cure, good flexural strength, good adhesion to dentin and enamel, and high fluoride release, even when cured in thick sections and in the dark.

40 Claims, 1 Drawing Sheet

FIG. 1

GLASS IONOMER CEMENT

TECHNICAL FIELD

This invention relates to water-based medical and dental cements.

BACKGROUND OF THE INVENTION

Fluoroaluminosilicate glass cements (also known as "glass ionomer cements") are used extensively in restorative dentistry. Two major classes of such cements are in current use. The first class is known as conventional glass ionomers. Conventional glass ionomers typically employ as their main ingredients a homopolymer or copolymer of an $\alpha,\beta$-unsaturated carboxylic acid (e.g., poly acrylic acid, copoly (acrylic, itaconic acid), etc.), a fluoroaluminosilicate ("FAS") glass, water, and chelating agent such as tartaric acid. Conventional glass ionomers typically are supplied in powder/liquid formulations that are mixed just before use. The mixture will undergo self-hardening in the dark due to an ionic reaction between the acidic repeating units of the polycarboxylic acid and cations leached from the glass.

The second major class of glass ionomer cements is known as resin-modified glass ionomer ("RMGI") cements. Like a conventional glass ionomer, an RMGI cement employs an FAS glass. However, the organic portion of an RMGI is different. In one type of RMGI, the polycarboxylic acid is modified to replace or end-cap some of acidic repeating units with pendent curable groups and a photoinitiator is added to provide a second cure mechanism, e.g., as in U.S. Pat. No. 5,130,347. Acrylate or methacrylate groups are usually employed as the pendant curable group. A redox cure system can be added to provide a third cure mechanism, e.g., as in U.S. Pat. No. 5,154,762. In another type of RMGI, the cement includes a polycarboxylic acid, an acrylate or methacrylate-functional monomer and a photoinitiator, e.g., as in Mathis et al., "Properties of a New Glass Ionomer/Composite Resin Hybrid Restorative", Abstract No. 51, J. Dent Res., 66:113 (1987) and as in U.S. Pat. Nos. 5,063,257, 5,520,725, 5,859,089 and 5,962,550. Photoinitiator cure systems have been said to be preferred (see, e.g., U.S. Pat. Nos. 5,063,257 and 5,859,089). Conventional peroxide oxidation agents have been noted to be unstable in ionomer cements (see, e.g., U.S. Pat. No. 5,520,725). Some patents exemplify RMGI cements that include a polycarboxylic acid, an acrylate or methacrylate-functional monomer and a redox or other chemical cure system (see, e.g., U.S. Pat. Nos. 5,520,725 and 5,871,360). Various monomer-containing or resin-containing cements are also shown in U.S. Pat. Nos. 4,872,936, 5,227,413, 5,367,002 and 5,965,632. RMGI cements are usually formulated as powder/liquid or paste/paste systems, and contain water as mixed and applied. They harden in the dark due to the ionic reaction between the acidic repeating units of the polycarboxylic acid and cations leached from the glass, and commercial RMGI products typically also cure on exposure of the cement to light from a dental curing lamp.

There are many important benefits of using glass ionomer cements. Fluoride release from glass ionomers tends to be higher than from other classes of cements such as metal oxide cements, compomer cements (anhydrous light-curable single-part paste systems containing FAS glass, as shown in Published PCT Application No. WO 97/18792 and U.S. Pat. Nos. 5,859,089, 5,962,550 and 6,126,922) or fluoridated composites, and thus glass ionomer cements are associated with cariostatic behavior. Although differences exist between commercial brands of glass ionomer cements, in general it is believed that high fluoride release leads to better cariostatic protection. Another important reason for using glass ionomer cements is the very good clinical adhesion of such cements to tooth structure, thus providing highly retentive restorations. Because conventional glass ionomers do not need an external curing initiation mode, they can be placed in bulk as a filling material in deep restorations, without requiring layering. However, conventional glass ionomers are rather technique sensitive (e.g., the performance can depend on the mixture ratio and the manner and thoroughness of mixing) and are quite brittle as evidenced by their low flexural strength. Thus restorations made from conventional glass ionomer cement mixtures tend to undergo fracture quite readily. Cured RMGIs have increased flexural strength and are less prone to mechanical fracture than conventional glass ionomer cements.

SUMMARY OF THE INVENTION

Photocurable RMGIs typically are placed in layers to overcome the light attenuation that accompanies increased thickness. This attenuation can be offset somewhat by instead or in addition employing a dark-curing chemical cure mechanism (such as the three-way cure mechanism shown in the above-mentioned U.S. Pat. No. 5,154,762 or the two-way or three-way cure mechanisms shown in the above-mentioned U.S. Pat. Nos. 5,520,725 and 5,871,360). However, for highly viscous RMGI cement mixtures it usually is necessary to perform a preliminary tooth priming or conditioning step in which a low viscosity aqueous-organic conditioner or primer is applied to the tooth prior to placement of the RMGI mix. Thus an additional step is required to obtain a clinically desirable restoration.

Neither conventional glass ionomers nor RMGIs have entirely satisfactory properties, and further improvements in the performance and ease of use of glass ionomer cements would be desirable.

The present invention provides, in one aspect, a glass ionomer cement comprising a mixture of a polymer having a plurality of acidic repeating units but being substantially free of polymerizable vinyl groups ("Polymer A") and a polymer having a plurality of acidic repeating units and a plurality of polymerizable vinyl groups ("Polymer B"). Preferably the cements of the invention comprise:
  a) Polymer A;
  b) Polymer B;
  c) FAS glass;
  d) redox cure system that can initiate dark cure of the vinyl groups; and
  e) water.

The invention also provides methods for making and using glass ionomer cements.

Preferred embodiments of the cements of the invention can be used without requiring a preliminary tooth priming or conditioning step and without requiring a curing lamp. The cements offer ease of mixing, convenient viscosity, convenient cure, good flexural strength, good adhesion to dentin and enamel, and high fluoride release, even when cured in thick sections and in the dark.

DETAILED DESCRIPTION

As used in connection with this invention, the term "polymer" includes molecules whose backbone is derived from one monomer (viz. a homopolymer) or from two or more monomers (viz., a copolymer). A polymer typically has a weight average molecular weight of at least about 2000.

Polymer A has a plurality of acidic repeating units but is substantially free of vinyl groups, that is, Polymer A has a sufficiently small number of vinyl groups so that it will not harden when combined with the redox cure system and water. Preferably, Polymer A contains less than about 1 mole percent vinyl groups. The acidic repeating units in Polymer A can be carboxyl or other acid groups (e.g., oxyacids of atoms such as boron, phosphorus and sulfur) that in the presence of water and the FAS glass will react with cations eluted from the glass and form a hardened cement composition. Polymer A need not be entirely water-soluble, but it should be at least sufficiently water-miscible (e.g., at least 2 weight percent or more) so that Polymer A does not undergo substantial sedimentation when combined with the other liquid ingredients of the cement. Polymer A can be formed in a variety of ways, from a variety of materials. A preferred form of Polymer A comprises a polymer of an $\alpha,\beta$-unsaturated carboxylic acid. Such polymers include but are not limited to polymers of acrylic acid, 2-chloroacrylic acid, 2-cyanoacrylic acid, aconitic acid, citraconic acid, fumaric acid, glutaconic acid, itaconic acid, maleic acid, mesaconic acid, methacrylic acid, tiglic acid and mixtures or copolymers thereof. Suitable Polymer A materials are also available from a wide variety of commercial sources, and many are found in currently available glass ionomer cements such as KETAC-FIL™ (3M ESPE Dental Products), FUJI II™ and FUJI IX™ (G-C Dental Industrial Corp.) and CHEM-FIL™ Superior (Dentsply International). Preferably, Polymer A comprises polyacrylic acid, an acrylic acid:itaconic acid copolymer or an acrylic acid:maleic acid copolymer. The substitution or addition of polymers or copolymers of other carboxylic acids can provide altered toughness and altered set time. Copolymers of $\alpha,\beta$-unsaturated carboxylic acids with small amounts of other non-acidic monomers, e.g., N-vinyl pyrrolidone, or with various acrylate-terminated polyethers, or with esters of $\alpha,\beta$-unsaturated carboxylic acids (e.g., methyl methacrylate) and the like may also be used. As will be appreciated by those skilled in the art, Polymer A should have a molecular weight sufficient to provide good storage, handling and mixing properties. A preferred molecular weight for Polymer A is about 3000 to about 300,000 weight average molecular weight as evaluated using gel permeation chromatography and a polystyrene standard, with about 10,000 to about 150,000 being most preferred. The cement should contain a sufficient quantity of Polymer A in order to provide the desired setting or hardening rate and desired overall properties following hardening. Preferably the mixed but unset cements of the invention contain about 0.5 to about 30 percent by weight, more preferably about 0.5 to about 20 percent by weight, and most preferably about 1 to about 10 percent by weight of Polymer A, based on the total weight (including water) of the mixed but unset cement components.

Polymer B has a plurality of acidic repeating units and a plurality of polymerizable vinyl groups. The acidic repeating units can be like those described above for Polymer A. The vinyl groups enable Polymer B to polymerize in the presence of the redox cure system. Polymer B need not be entirely water-soluble, but it should be at least sufficiently water-miscible (e.g., at least 5 weight percent or more) so that it does not undergo substantial sedimentation when combined with the other liquid ingredients of the cement. Polymer B can be formed in a variety of ways, from a variety of materials. One convenient method for forming Polymer B involves partially reacting a material suitable for use as Polymer A (or suitable for use as a Polymer A precursor such as a polymeric acid anhydride) with a monomer containing an acid- or acid anhydride-reactive group and containing one or more vinyl groups that will provide the desired polymerizable functionality in Polymer B. The acid- or acid anhydride-reactive group reacts with acid units on Polymer A (or with anhydride units in a polymeric acid anhydride precursor to Polymer A) to provide pendant vinyl groups in the resulting reaction product. Another convenient method for forming Polymer B involves copolymerizing a suitable $\alpha,\beta$-unsaturated carboxylic acid and a suitable $\alpha,\beta$-unsaturated monomer containing one or more such pendant vinyl groups. Preferably the Polymer B vinyl groups are acrylate or methacrylate groups. Most preferably the Polymer B vinyl groups are linked to the polymer backbone through an amide linkage of other suitable organic linking group. Other suitable groups include but are not limited to styryl ($CH_2$:$CHC_6H_5$) groups, allyl ($CH_2$:$CHCH_2$—) groups and other groups that will be familiar to those skilled in the art. Preferably, the number of acidic repeating units and vinyl groups is adjusted to provide an appropriate balance of properties in the cement, both during and after cement hardening. Polymers containing about 70 to about 90 mole % acidic repeating units and about 10 to about 30 mole % vinyl groups are preferred. Suitable embodiments of Polymer B include but are not limited to those described in U.S. Pat. Nos. 4,872,936, 5,130,347 and 5,227,413. Suitable Polymer B materials can be found in currently available RMGI cements such as VITREMER™ and VITREBOND™ (3M ESPE Dental Products). These cements contain Polymer B but no Polymer A. Preferably, Polymer B comprises an acrylic acid:itaconic acid copolymer that has been partially reacted with isocyanatoethyl methacrylate as shown in U.S. Pat. No. 5,130,347. As will be appreciated by those skilled in the art, Polymer B should have a molecular weight sufficient to provide good storage, handling and mixing properties. A preferred molecular weight for Polymer B is about 3000 to about 300,000 weight average molecular weight, with about 10,000 to about 150,000 being most preferred. The cement should contain a sufficient quantity of Polymer B in order to provide the desired curing rate and desired overall properties following cure. Preferably the mixed but unset cements of the invention contain about 1 to about 30 percent by weight, more preferably about 1 to about 25 percent by weight, and most preferably about 5 to about 20 percent by weight of Polymer B, based on the total weight (including water) of the mixed but unset cement components.

The FAS glass preferably contains sufficient elutable cations so that a hardened cement will form when the glass is mixed with Polymer A and water. The glass also preferably contains sufficient elutable fluoride ions so that the hardened cement will have cariostatic properties. The glass can be made from a melt containing fluoride, alumina and other glass-forming ingredients using techniques familiar to those skilled in the FAS glassmaking art. The FAS glass preferably is in the form of particles that are sufficiently finely-divided so that they can conveniently be mixed with the other cement components and will perform well when the resulting mixture is used in the mouth. Preferred average particle diameters for the FAS glass are about 0.2 to about 15 micrometers, more preferably about 1 to 10 micrometers, as measured using, for example, a sedimentation analyzer. Suitable FAS glasses will be familiar to those skilled in the art, and are available from a wide variety of commercial sources, and many are found in currently available glass ionomer cements such as VITREMER™, VITREBOND™, RELY X™ LUTING CEMENT and KETAC-FIL™ (3M ESPE Dental Products), FUJI II™ and FUJI IX™ (G-C Dental Industrial Corp.) and CHEMFIL™ Superior (Dentsply International). The FAS glass can optionally be subjected to a surface treatment. Suitable surface treatments include but are not limited to acid washing (e.g., treatment with a phosphoric acid), treatment with a phosphate, treatment with a chelating agent such as tartaric acid, and treatment with a silane or an acidic or basic silanol solution. Desirably the pH of the treating solution or the treated glass is adjusted to neutral or near-neutral, as this can increase storage stability of the cement. The resulting treated glass can be used in cements containing FAS glass, Polymer A and Polymer B, and can also be used in cements containing FAS glass and Polymer A alone, or FAS glass and Polymer B alone.

The cement should contain a sufficient quantity of FAS glass in order to provide the desired curing rate and desired overall properties following cure. Preferably the mixed but unset cements of the invention contain less than about 90%, more preferably about 25% to about 85%, and most preferably about 45% to about 75% by weight of FAS glass, based on the total weight (including water) of the mixed but unset cement components.

The redox cure system promotes cure of the vinyl groups on Polymer B when the cement components are mixed. The cure is a dark reaction, that is, it not dependent on the presence of light and can proceed in the absence of light. A variety of redox cure systems can be employed in the invention. Typically these systems employ a reducing agent and an oxidizing agent. The reducing agent and oxidizing agent preferably are soluble in the combination of liquid components of the mixed cement. Useful reducing agents and oxidizing agents include but are not limited to those shown in "Redox Polymerization", G. S. Misra and U. D. N. Bajpai, *Prog. Polym. Sci.,* 8, 61–131 (1982). The reducing agent and oxidizing agent preferably are also sufficiently shelf-stable and free of undesirable colorization to permit their storage and use under typical dental conditions. Suitable reducing agents will be familiar to those skilled in the art, and include but are not limited to ascorbic acid, cobalt (II) chloride, ferrous chloride, ferrous sulfate, hydrazine, various amines, hydroxylamine (depending upon the choice of oxidizing agent), oxalic acid, thiourea, and derivatives of oxyacids of sulfur at an oxidation state of V or less. Derivatives of oxyacids of sulfur at an oxidation state of IV are particularly useful. Suitable oxidizing agents will also be familiar to those skilled in the art, and include but are not limited to cobalt (III) chloride, tert-butyl hydroperoxide, ferric chloride, hydroxylamine (depending upon the choice of reducing agent), perboric acid and its salts, and salts of a permanganate or persulfate anion. Hydrogen peroxide can also be used, although it may interfere with a photoinitiator if present in the cement. In some instances oxygen (e.g., from adventitious air) can act as the oxidant, particularly if the reducing agent comprises at least one oxyacid of sulfur IV or its derivative. It may also be desirable to use more than one oxidizing agent or more than one reducing agent. Small quantities of transition metal compounds may also be added to accelerate the rate of redox cure. The amount of reducing agent and oxidizing agent should be sufficient to provide the desired degree of polymerization of Polymer B. Preferably the mixed but unset cements of the invention contain a combined weight of about 0.01 to about 10%, more preferably about 0.2 to about 5%, and most preferably about 0.5 to about 5% of the reducing agent and oxidizing agent, based on the total weight (including water) of the mixed but unset cement components. The reducing agent or the oxidizing agent can be microencapsulated as described in U.S. Pat. No. 5,154,762. This will generally enhance shelf stability of the cement parts and if necessary permit packaging both the reducing agent and oxidizing agent together. For example, through appropriate selection of an encapsulant, both the oxidizing agent and reducing agent can be combined with the FAS glass and kept in a storage-stable state. Likewise, through appropriate selection of a water-insoluble encapsulant, the reducing agent and oxidizing agent can be combined with Polymer A, Polymer B and water and maintained in a storage-stable state. Preferably the encapsulant is a medically acceptable polymer and a good film former. Also, the glass transition temperature (Tg) of the encapsulant preferably is above room temperature.

Photoinitiators can also be added to the cement but are not required. The photoinitiator should be capable of promoting polymerization of the vinyl groups on Polymer B (e.g., capable of promoting free-radical crosslinking of an $\alpha,\beta$-unsaturated group) on exposure to light of a suitable wavelength and intensity. The photoinitiator preferably is sufficiently shelf-stable and free of undesirable coloration to permit its storage and use under typical dental conditions. Visible light photoinitiators are preferred. The photoinitiator preferably is water-soluble or water-miscible. Photoinitiators bearing polar groups usually have a sufficient degree of water-solubility or water-miscibility. The photoinitiator frequently can be used alone but typically it is used in combination with a suitable donor compound or a suitable accelerator (for example, amines, peroxides, phosphorus compounds, ketones and alpha-diketone compounds). Suitable visible light-induced and ultraviolet light-induced initiators will be familiar to those skilled in the art. Combinations of an alpha-diketone (e.g., camphorquinone) and a diaryliodonium salt (e.g., diphenyliodonium chloride, bromide, iodide or hexafluorophosphate) with or without additional hydrogen donors (such as sodium benzene sulfinate, amines and amine alcohols) are particularly preferred. If employed, the photoinitiator should be present in an amount sufficient to provide the desired rate of photopolymerization. This amount will be dependent in part on the light source, the thickness of the cement layer to be exposed to radiant energy and the extinction coefficient of the photoinitiator. Preferably, mixed but unset photocurable cements of the invention will contain about 0.01 to about 5%, more preferably from about 0.1 to about 2% photoinitiator, based on the total weight (including water) of the mixed but unset cement components.

The cements of the invention contain water. The water can be present in the cement as sold, or (less preferably) added by the practitioner just prior to mixing and use. Unlike a compomer, appreciable water is present in the cement as applied. The water can be distilled, deionized or plain tap water. Generally, deionized water is preferred. The amount of water should be sufficient to provide adequate handling and mixing properties and to permit the transport of ions in the reaction between the FAS glass and the acidic repeating units on Polymer A and Polymer B. Preferably, water represents about 0.5% to about 40%, more preferably about 1% to about 30%, and most preferably about 5% to about 20% of the total weight of ingredients used to form the mixed but unset cement.

The cements of the invention can if desired also contain one or more solvents, diluents or $\alpha,\beta$-unsaturated monomers. Suitable solvents or diluents include but are not limited to alcohols such as ethanol and propanol. The addition of α,β-unsaturated monomers can provide altered properties such as toughness, adhesion, set time and the like. If α,β-unsaturated monomers are employed, they preferably are water-soluble, water-miscible or water-dispersible. Water-soluble, water-miscible or water-dispersible acrylates and methacrylates such as 2-hydroxyethyl methacrylate, 2-hydroxypropyl methacrylate, tetrahydrofurfuryl methacrylate, glycerol mono- or di-methacrylate, trimethylol propane trimethacrylate, ethylene glycol dimethacrylate, polyethylene glycol dimethacrylate, urethane methacrylates, acrylamide, methacrylamide, methylene bis-acrylamide or methacrylamide, and diacetone acrylamide and methacrylamide are preferred. Other α,β-unsaturated acidic monomers such as glycerol phosphate monomethacrylates, glycerol phosphate dimethacrylates, hydroxyethyl methacrylate phosphates, citric acid di- or tri-methacrylates and the like may also be used as reactive diluents. Mixtures of α,β-unsaturated monomers can be added if desired. Preferably, the mixed but unset components of the invention will contain a combined weight of about 0.5 to about 40%, more preferably about 1 to about 30%, and most preferably about 5 to about 20% water, solvents, diluents and α,β-unsaturated monomers, based on the total weight (including such water, solvents, diluents and α,β-unsaturated monomers) of the mixed but unset cement components.

The cements of the invention can also contain non-fluoride-releasing fillers. These fillers can be acid-reactive or non-acid-reactive. Like the FAS glass, the non-fluoride-releasing fillers preferably are sufficiently finely-divided so that they can conveniently be mixed with the other ingredients and used in the mouth. Suitable acid-reactive fillers include but are not limited to metal oxides and hydroxides, metal salts that will react with the acidic repeating units on Polymer A or Polymer B, and non-fluoride-releasing glasses that contain an elutable multivalent cation such as strontium, calcium, zinc, aluminum, iron or zirconium. Suitable metal oxides include but are not limited to barium oxide, calcium oxide, magnesium oxide and zinc oxide and the like. Suitable metal hydroxides barium hydroxide, calcium hydroxide, magnesium hydroxide, zinc hydroxide and the like. Suitable metal salts include but are not limited to salts of multivalent cations, for example aluminum acetate, aluminum chloride, calcium chloride, magnesium chloride, zinc chloride, aluminum nitrate, barium nitrate, calcium nitrate, magnesium nitrate and strontium nitrate. Suitable glasses include but are not limited to borate glasses and phosphate glasses. Suitable non-acid-reactive fillers include but are not limited to fumed silica, barium aluminosilica, zirconia-silica microspheres and ground quartz. Non-acid-reactive fillers are especially useful in paste/paste formulations. Suitable acid-reactive and non-acid-reactive fillers will be familiar to those skilled in the art and are available from a variety of commercial sources. If desired, the filler can be subjected to a surface treatment such as those described above for FAS glass. The amount of filler should be sufficient to provide the desired mixing and handling properties before cure, and good performance after cure, but should not be so large as to prevent incorporation of sufficient FAS glass to provide the desired degree of cariostatic activity. Preferably, the filler represents less than about 50%, more preferably less than about 40%, and most preferably from 0% to about 30% by weight of the total weight (including water) of the unset cement components.

If desired, the cements of the invention can contain other typical ionomer adjuvants such as pigments, chelating agents, surfactants, rheology modifiers and the like. The types and amounts of such adjuvants will be apparent to those skilled in the art.

The cements of the invention can be supplied in a variety of forms including two-part powder/liquid, paste/liquid and paste/paste systems. Other forms employing combinations of two or more parts each of which is in the form of a powder, liquid, gel or paste are also possible. In such multi-part systems, Polymer A and B could be contained in separate parts of the cement or contained in only one part of the cement. As an example of a multi-part system, the FAS glass and Polymer A or Polymer B can be included in a first anhydrous part, and water can be included in a second part. For example, in a powder/liquid system, a powder containing the FAS glass and optionally containing a lyophilized (e.g., freeze-dried) or other anhydrous form of Polymer A or Polymer B (or both Polymer A and Polymer B) can be combined with a liquid containing Polymer B, Polymer A, (or both Polymer B and Polymer A) and water. The redox cure system can be added to one or both of the powder and the liquid, and encapsulated as needed to prevent premature reaction. Typically the cement will be sold in the form of a sealed kit containing the cement ingredients packaged in suitably-designed containers, together with instructions for use of the cement and optionally one or more suitably-designed auxiliary devices (e.g., mixing or dispensing devices) that help a practitioner to prepare and use the cement.

As an example of a paste/liquid system, the paste can contain the FAS glass and the liquid can contain water. For instance, the paste can contain the FAS glass and a suitable α,β-unsaturated monomer or reactive oligomer and the liquid can contain Polymer A, Polymer B, water and optionally a suitable α,β-unsaturated monomer or oligomer. The redox cure system can be added to one or both of the paste and the liquid, and encapsulated as needed to prevent premature reaction.

As an example of a paste/paste system, the FAS glass can be included in the first paste and Polymer B can be included in the second paste. For instance, the first paste can include the FAS glass and a suitable α,β-unsaturated monomer, and the second paste can include Polymer A, Polymer B, water, a non-acid-reactive filler and optionally a suitable α,β-unsaturated monomer. The redox cure system can be added to any or all of such pastes, and encapsulated as needed to prevent premature reaction.

The cements of the invention can be mixed and clinically applied using conventional techniques. A curing light is not required or desired (unless a photoinitiator has been included in the cement). The cements can provide the convenience of conventional self-cure glass ionomers yet provide the improved physical properties characteristic of light-cure or tri-cure glass ionomers. The cements can provide very good adhesion to dentin and enamel, without requiring hard tissue pretreatment. The cements can also provide very good long-term fluoride release. Hence the cements of the invention provide glass ionomer cements that can be cured in bulk without the application of light or other external curing energy, do not require a pre-treatment, have improved physical properties including improved flexural strength, and have high fluoride release for cariostatic effect. The cements will have particular utility in clinical applications where cure of a conventional light-curable cement may be difficult to achieve. Such applications include but are not limited to deep restorations, large crown build-ups, endodontic restorations, attachment of orthodontic brackets (including pre-coated brackets, where for example a paste portion could be pre-applied to the bracket and a liquid portion could later be brushed onto a tooth), bands, buccal tubes and other devices, luting of metallic crowns or other light-impermeable prosthetic devices to teeth, and other restorative applications in inaccessible areas of the mouth. The combination of an ionic hardening reaction between the FAS glass and acidic repeating units on Polymer A and Polymer B, plus a separate redox curing dark reaction involving the vinyl groups on Polymer B, facilitates thorough, uniform cure and retention of good clinical properties. The cements of the invention thus show good promise as a universal restorative.

The cements can also be provided in the form of preformed cured articles that can be ground or otherwise formed into a custom-fitted shape by the dentist or other user.

The cements of the invention are further described in the following illustrative examples, which show various powder/liquid systems. The manner in which other systems would be prepared will readily be understood by those skilled in the art. In formulating any such systems, care should be taken to avoid combinations that might cause premature curing reactions to take place during storage of the components prior to mixing and use. The examples shown below employ a relatively large portion of FAS glass, and thus are relatively viscous. These relatively viscous formulations may be especially useful for use in an atraumatic restorative technique ("ART", see "Atraumatic Restorative Treatment", J. Frencken, T. Pilot, Y. Songpaisan, P. Phantumvanit, *Journal of Public Health Dentistry,* 56, No. 3 (Special issue 1996) or a minimal intervention ("MI") restorative technique (see M. Tyas, K. Anusavice, J. Frencken, G. Mount, "Minimal Intervention Dentistry—a Review", FDI Commission Project 1-97, *International Dental Journal,* 50:1–12 (2000)). Straightforward alterations in the formulations shown below will provide other formulations (e.g., more or less viscous formulations) suitable for a host of other dental and orthodontic applications. Unless otherwise indicated, all parts and percentages are on a weight basis and all water is deionized water.

The following abbreviations for starting materials were employed:

| | |
|---|---|
| AA:ITA | Polymer A, made from a 4:1 mole ratio copolymer of acrylic acid:itaconic acid, prepared according to Example 3 of U.S. Pat. No. 5,130,347, Mw (avg) = 106,000; polydispersity $\rho$ = 4.64. |
| AA:IA:IEM | Polymer B, made by reacting AA:ITA with sufficient 2-isocyanatoethyl methacrylate to convert 16 mole percent of the acid groups of the copolymer to pendent methacrylate groups, according to the dry polymer preparation of Example 11 of U.S. Pat. No. 5,130,347. |
| BHT | Butylated hydroxytoluene. |
| EPS | Encapsulated potassium persulfate, prepared according to Example 9 of U.S. Pat. No. 5,154,762. |
| FAS I | An ascorbic acid-treated FAS glass powder like Glass A of Example 1 of U.S. Pat. No. 5,154,762 (but having a surface area of 2.8 m$^2$/g) was silane-treated with a liquid treatment solution. The treatment solution had been prepared by combining 4 parts A174 $\gamma$-methacryloxypropyl trimethoxysilane (CK Witco Corp.) and 40 parts water, adding glacial acetic acid to obtain a pH of 3.01, and stirring for 0.5 hours. The resultant clear treatment solution was mixed with 100 parts of the glass powder to provide a slurry. The slurry was stirred for 1.5 hours, poured into tray lined with TEFLON ™ polytetrafluoroethylene (DuPont) and dried for 16 hours at 80° C. The resulting dried cake was crushed by sifting it through a 60 micrometer sieve. |
| FAS II | An FAS glass like FAS I was prepared but sifted through a 74 micrometer sieve. |
| FAS III | The glass frit of Example 1 of U.S. Pat. No. 5,154,762 was ground to a surface area of 84 m$^2$/g and silane-treated with a liquid treatment solution. The treatment solution had been prepared by combining 32 parts A174 $\gamma$-methacryloxypropyl trimethoxysilane (CK Witco Corp.), 224 parts water and 32 parts glacial acetic acid, and stirring for 0.5 hours. The resultant clear treatment solution was mixed with 400 parts of the glass powder to provide a slurry. After 30 minutes of mixing the pH was adjusted to 6.7 by adding ammonium hydroxide. The mixture was then poured into a glass tray and dried for 17 hours at 80° C. The resulting dried cake was crushed by sifting it through a 74 micrometer sieve. |
| FAS IV | FAS IV was like FAS I but without silane treatment. |
| FAS V | 50/50 Blend of FAS II and IV. |
| GDMA | Glyceryl dimethacrylate. |
| HEMA | 2-Hydroxyethyl methacrylate. |
| PS | Finely ground potassium persulfate. |
| STS | Sodium p-toluene sulfinate. |

The following abbreviations for measurements were employed:

| | |
|---|---|
| CS | Compressive strength, evaluated by first injecting the mixed cement samples into a glass tube having a 4 mm inner diameter. The ends of the sample were plugged with silicone plugs. The filled tubes were subjected to 0.275 MPa pressure for 5 minutes. For light-cured cement specimens, the samples were cured by radial exposure to two XL3000 ™ dental curing lights (3M) while still under pressure. For self-cured cement specimens, the samples were instead placed in a chamber at 37° C. and ≧90% relative humidity and allowed to stand for 1 hour. The cured samples were next placed in 37° C. water for 1 day, and then cut to a length of 8 mm. Compressive strength was determined according to ISO Standard 7489 using an INSTRON ™ universal tester (Instron Corp.) operated at a crosshead speed of 1 mm/min. |
| DA | Dentin adhesion, measured according to the procedure described in U.S. Pat. No. 5,154,762, but without using any pretreatment of the dentin. |
| DTS | Diametral tensile strength, measured using the above-described CS procedure but using samples cut to a length of 2 mm. |
| EA | Enamel adhesion, measured according to the procedure described in U.S. Pat. No. 5,154,762. |
| FR | Fluoride release, was evaluated in vitro by mixing samples of the cements and placing them in a 20 mm diameter x 1 mm high cylindrical mold capped with two plastic sheets clamped under moderate pressure using a C-clamp. The cements were allowed to cure for 20 minutes, and then stored in a humidity chamber for one hour. The samples were removed from the chamber and each specimen immersed separately in a vial containing 25 ml of water in a 37° C. oven for varying periods of time. At each measurement interval, a specimen vial was removed from the oven and 10 ml of the water was measured out from the specimen vial and combined with 10 ml of TISAB II ™ Total Ionic Strength Adjustment Buffer (Sigma Aldrich). The resulting mixture was stirred and measured using a fluoride ion selective electrode to determine the cumulative micrograms of fluoride leached per gram of the cement for the applicable measurement period, using an average of three samples. The vials were replenished with fresh deionized water and returned to the oven until the next measurement period. |
| FS | Flexural strength, evaluated by placing the mixed cement samples in a 2 mm x 2 mm x 25 mm mold made of TEFLON ™ polytetrafluoroethylene (DuPont). The filled mold was sandwiched between two polyester sheets and clamped between the jaws of a C-clamp. The assembly was placed in a chamber at 37° C. and ≧90% relative humidity and allowed to stand for 10 minutes. The C-clamp was removed and the mold was allowed to stand in the chamber for an additional hour. The samples were next placed in 37° C. water for 1 day. The cured cement was then removed from the mold, sanded to make the sample flat and then tested for flexural strength using a three-point bend test carried out according to ISO Standard 4049. The crosshead speed of the INSTRON testing machine was 0.75 mm/min and the distance between the two lower supports was about 20 mm. |
| RH | Relative humidity. |

EXAMPLE 1

A liquid portion was formulated by mixing 12.5 parts AA:ITA, 12.5 parts AA:ITA:IEM, 5 parts HEMA and 20 parts water until the components dissolved. A powder portion was formulated by tumbling together 100 parts FAS I, 1.2 parts STS and 1 part PS. The powder portion and liquid portion were hand-spatulated at a 2.7:1 powder/liquid ratio and allowed to self-cure in a mold described in ISO Standard 9917, without use of a dental curing lamp. The set time was evaluated using a 400 g indenter. The cement had a set time of 2 minutes, 55 sec; CS of 162 MPa; DTS of 28 MPa; DA of 4.2 MPa and an EA of 6.2 MPa. These values represent excellent physical properties and performance.

EXAMPLE 2

Using the method of Example 1, a liquid portion was formulated by mixing 12.5 parts AA:ITA, 12.5 parts AA:ITA:IEM, 5 parts GDMA and 20 parts water until the components dissolved. The resulting liquid portion and the powder portion of Example 1 were hand-spatulated at a 2.7:1 powder/liquid ratio and allowed to self-cure. The cement had a set time of 3 minutes, 15 sec; CS of 145 MPa; DTS of 27 MPa; FS of 58 MPa; DA of 4.5 MPa and an EA of 8.0 MPa. These values represent excellent physical properties and performance.

EXAMPLE 3

Using the method of Example 1, a liquid portion was formulated by mixing 14.4 parts AA:ITA, 35.6 parts AA:ITA:IEM, 17.1 parts HEMA, 0.06 parts BHT and 32.9 parts water until the components dissolved. The resulting liquid portion and the powder portion of Example 1 were hand-spatulated at a 2.7:1 powder/liquid ratio and allowed to self-cure. The cement had a set time of 3 minutes, 35 sec; CS of 173 MPa; DTS of 32 MPa; FS of 60 MPa; DA of 5.1 MPa and an EA of 9.1 MPa. These values represent excellent physical properties and performance.

EXAMPLE 4

Using the method of Example 1, a powder portion was formulated by mixing 100 parts FAS III, 1.2 parts STS and 2 parts EPS. The resulting powder portion and the liquid portion of Example 3 were hand-spatulated at a 2.7:1 powder/liquid ratio and allowed to self-cure. The cement had a set time of 3 minutes, 10 sec; CS of 189 MPa; DTS of 33 MPa; FS of 62 MPa; DA of 4.11 MPa and an EA of 5.57 MPa. These values represent excellent physical properties and performance.

EXAMPLE 5

Using the method of Example 1, a powder portion was formulated by mixing 100 parts FAS IV, 1.2 parts STS and 2 parts EPS. The resulting powder portion and the liquid portion of Example 3 were hand-spatulated at a 2.5:1 powder/liquid ratio and allowed to self-cure. The cement had a set time of 3 minutes, 15 sec; CS of 210 MPa, DTS of 41 MPa, DA of 4.11 MPa, FS of 58 MPa, DA of 5.19 MPa and EA of 9.57 MPa. These values represent excellent physical properties and performance.

The powder portion was aged in an open container at 90% RH and 37° C. for two months, then mixed with the liquid portion to reevaluate the physical properties of the cement after a 2 month aging period. As shown below in Table 1, the aged powder gave very similar properties to the initial powder.

TABLE 1

| Aging Interval | Aging conditions | Set Time, min:sec | CS, MPa | DTS, MPa | DA, MPa | EA, MPa |
| --- | --- | --- | --- | --- | --- | --- |
| Initial | Ambient | 3:20 | 210 | 41 | 5.19 | 9.57 |
| 2 Weeks | 37° C./90 RH % | 3:25 | 196 | 37 | 5.53 | 7.01 |
| 1 Month | 37° C./90 RH % | 3:45 | 188 | 37 | 4.33 | 9.43 |
| 2 Months | 37° C./90 RH % | 4:00 | 198 | 37 | 4.56 | 9.48 |

Figure 1:
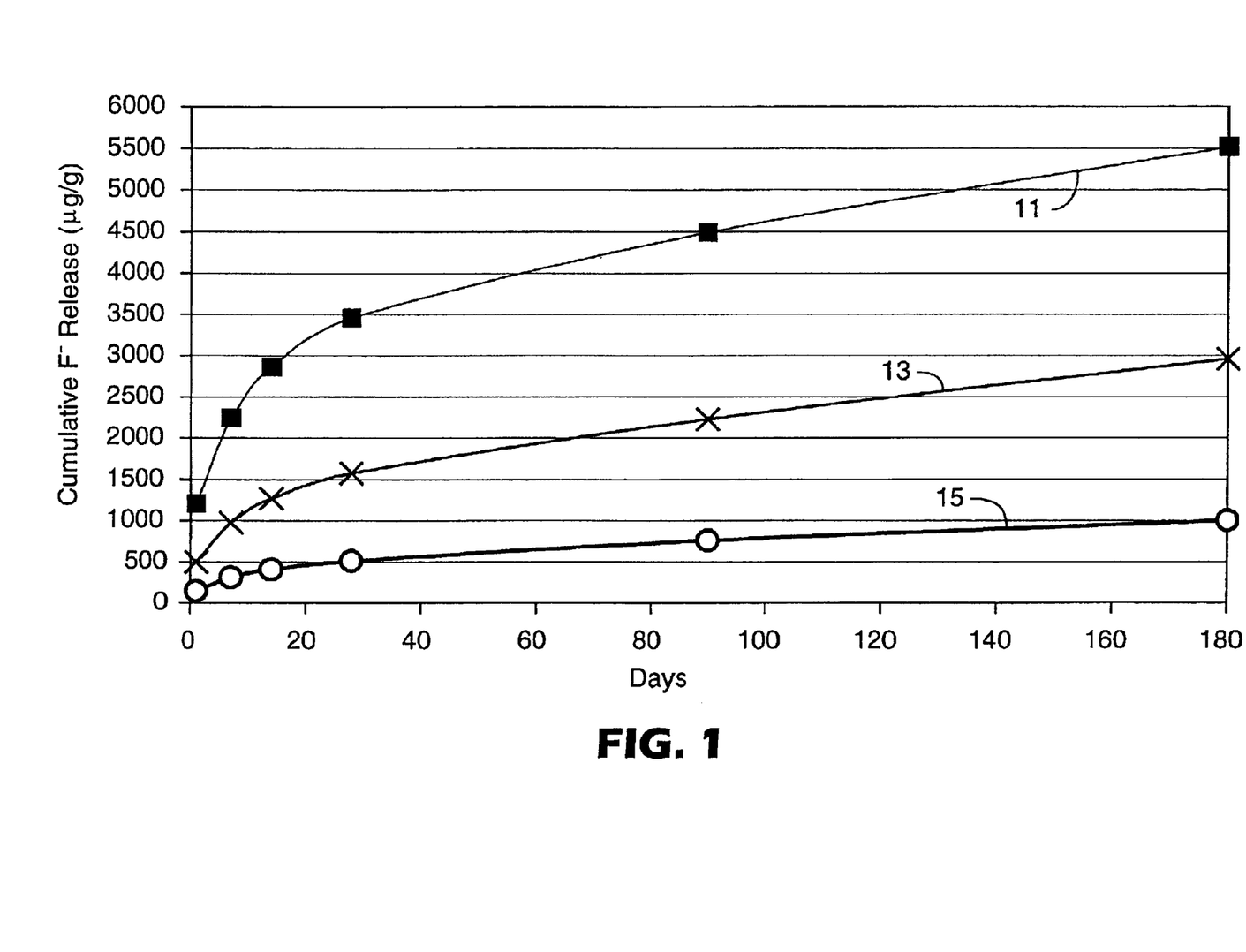
FIG. 1 is a graph showing fluoride release vs. time for a cement of the invention and two comparison cements.

Fluoride Release of the cement was evaluated and compared to two commercially available glass ionomer materials. The results are shown in FIG. 1, which shows the cumulative fluoride release over a 6 month time span for the cement of Example 5, VITREMER™ RMGI cement (3M ESPE) and FUJI IX™ conventional glass ionomer cement (G-C Dental Industrial Corp.) as curves 11, 13 and 15, respectively. As shown in FIG. 1, the cement of Example 5 provided higher fluoride release than the two commercial glass ionomer cements. In addition, unlike the RMGI cement, the cement of Example 5 did not require use of a curing light. Also, unlike both the commercial cements, the cement of Example 5 did not require use of a tooth pretreatment.

COMPARATIVE EXAMPLE 1

Using the method of Example 1, a liquid portion was formulated by mixing 50 parts AA:ITA, 45 parts water and 5 parts tartaric acid until the components dissolved. The resulting liquid portion and the non-silane treated precursor of FAS IV were hand-spatulated at a 2.7:1 powder/liquid ratio and allowed to self-cure. The resulting cement approximated a conventional glass ionomer, and had a set time of 3 minutes; CS of 173 MPa; DTS of 28 MPa and FS of 29 MPa. Thus although the CS and DTS values were relatively high, the FS value was not.

COMPARATIVE EXAMPLE 2

Following the manufacturer's directions, FUJI IX™ conventional glass ionomer cement was mixed and allowed to self-cure in a mold. The resulting cement had an FS of 31 MPa; a DA (without tooth pretreatment) of 2.4 MPa and an EA (also without tooth pretreatment) of 6.26 MPa. This represented a small increase in FS compared to Comparative Example 1 but was not as high as the FS values obtained for the cements of the invention reported above. In addition, the cements of the invention provided improved adhesion to untreated dentin and enamel.

COMPARATIVE EXAMPLE 3

Following the manufacturer's directions, VITREMER™ resin-modified glass ionomer cement (3M ESPE) was mixed and allowed to self-cure in a mold. The resulting cement had a DA (without tooth pretreatment) of zero MPa and an EA (also without tooth pretreatment) of 2.2 MPa. Again, the cements of the invention provided improved adhesion to untreated dentin and enamel.

EXAMPLES 6–14

Using the method of Example 1, a series of liquid portions was prepared by combining Polymer A (AA:ITA), Polymer B (AA:ITA:IEM), HEMA and water in the relative amounts shown below in Table 2. Each liquid also contained 0.06 parts BHT. The liquids had pH values between 3 and 4. A powder portion was formulated by mixing 100 parts FAS I, 1.2 parts STS and 1 part PS. The liquid portions and the powder portion were hand-spatulated at a 2.7:1 powder/liquid ratio and allowed to self-cure. The cements had set time, compressive strength, diametral tensile strength, dentin adhesion and enamel adhesion values as set out below in Table 2. Because these examples included endpoints for a designed experiment, some of the measured values were not as high as those obtained for the other cements of the invention reported above.

TABLE 2

| Example No. | AA:ITA | AA:ITA:IEM | HEMA | Water | Set Time, min:sec | CS, MPa | DTS, MPa | DA, MPa | EA, MPa |
| --- | --- | --- | --- | --- | --- | --- | --- | --- | --- |
| 6 | 35.6 | 14.4 | 2.94 | 47.1 | 2:25 | 132 | 21 | 2.94 | 3.96 |
| 7 | 14.4 | 35.6 | 2.94 | 47.1 | 2:15 | 129 | 23 | 1.64 | 3.82 |
| 8 | 35.6 | 14.4 | 17.1 | 32.9 | 3:30 | 157 | 27 | 1.96 | 5.64 |
| 9 | 14.4 | 35.6 | 17.1 | 32.9 | 3:35 | 173 | 32 | 2.42 | 7.27 |
| 10 | 25 | 25 | 0.01 | 50 | 2:00 | 118 | 19 | 1.07 | 2.31 |
| 11 | 25 | 25 | 20 | 30 | 4:10 | 155 | 24 | 2.86 | 7.57 |
| 12 | 40 | 10 | 10 | 40 | 3:00 | 133 | 22 | 2.86 | 4.04 |
| 13 | 10 | 40 | 10 | 40 | 2:30 | 160 | 29 | 2.38 | 7.11 |
| 14 | 25 | 25 | 10 | 40 | 2:35 | 156 | 26 | 2.38 | 5.25 |

The results in Table 2 show a range of liquid formulations and their effect on several physical properties of the cement.

EXAMPLE 15 AND COMPARATIVE EXAMPLES 4–7

Using the method of Example 1, a series of liquid portions was prepared by combining Polymer A (AA:ITA), Polymer B (AA:ITA:IEM), HEMA, water, tartaric acid and BHT in the relative amounts shown below in Table 3. A powder portion was formulated by mixing 100 parts FAS IV, 1.16 parts STS and 1.94 part EPS. The liquid portions and the powder portion were hand-spatulated at a 2.7:1 powder/liquid ratio and allowed to self-cure. The cements had set time, compressive strength, diametral tensile strength, flexural adhesion, dentin adhesion and fluoride release values as set out below in Table 3. The results in Table 3 show a synergistic increase in CS, DTS, FS and DA for a cement containing both Polymer A and Polymer B, together with very good fluoride release.

TABLE 3

| Example No. or Comp. Ex. No. | AA:ITA | AA:ITA:IEM | HEMA | Water | Tartaric Acid | BHT | Set Time, min:sec | CS, MPa | DTS, MPa | FS, MPa | DA, MPa | FR at 14 days, µg/g |
|---|---|---|---|---|---|---|---|---|---|---|---|---|
| 15 | 14.4 | 35.6 | 17.1 | 32.9 | 0 | 0.0625 | 3:50 | 201 | 39 | 66 | 4.97 | 803 |
| Comp.4 | 0 | 50 | 17.1 | 32.9 | 0 | 0.0625 | 3:20 | 197 | 36 | 55 | 1.11 | 621 |
| Comp.5 | 50 | 0 | 17.1 | 32.9 | 0 | 0.0625 | 3:40 | 112 | 22 | 26 | 0 | 1118 |
| Comp.6 | 50 | 0 | 0 | 50 | 0 | 0 | 3:50 | 137 | 16 | 24 | 0 | 320 |
| Comp.7 | 45 | 0 | 0 | 50 | 5 | 0 | 3:40 | 130 | 17 | 21 | 1.28 | 480 |

Various modifications and alterations of this invention will be apparent to those skilled in the art without departing from the scope and spirit of this invention. Thus this invention should not be restricted to that which has been set forth herein only for illustrative purposes.

I claim:

1. A glass ionomer cement comprising:
   a) polymer having a plurality of acidic repeating units but being substantially free of polymerizable vinyl groups;
   b) polymer having a plurality of acidic repeating units and a plurality of polymerizable vinyl groups;
   c) fluoroaluminosilicate glass;
   d) redox cure system that can initiate dark cure of the vinyl groups; and
   e) water.

2. A cement according to claim 1, wherein the fluoroaluminosilicate glass has been subjected to a surface treatment comprising acid, phosphate, chelating agent, silane or silanol.

3. A cement according to claim 2, wherein the glass has a neutral or near-neutral pH.

4. A cement according to claim 1, wherein at least one of the redox cure system components is encapsulated.

5. A cement according to claim 1, in the form of a multi-part product comprising fluoroaluminosilicate glass and the polymer that is substantially free of polymerizable vinyl groups in a first anhydrous part, and water in a second part.

6. A cement according to claim 1, in the form of a multi-part product comprising fluoroaluminosilicate glass and the polymer having a plurality of polymerizable vinyl groups in a first anhydrous part, and water in a second part.

7. A cement according to claim 1, in the form of a paste/liquid product that comprises fluoroaluminosilicate glass in the paste and water in the liquid.

8. A cement according to claim 1, in the form of a paste/paste product that comprises fluoroaluminosilicate glass in a first paste and a non-acid-reactive filler in a second paste.

9. A cement according to claim 1, comprising by weight about 0.5 to about 30 percent of the polymer that is substantially free of polymerizable vinyl groups, about 1 to about 30 percent of the polymer that has a plurality of polymerizable vinyl groups, less than about 90 percent of the fluoroaluminosilicate glass, about 0.01 to about 10 percent of the combined weight of the redox cure system and about 0.5 to about 40 percent of the combined weight of water and any added solvents, diluents or $\alpha,\beta$-unsaturated monomers.

10. A cement according to claim 1, comprising by weight about 0.5 to about 20 percent of the polymer that is substantially free of polymerizable vinyl groups, about 1 to about 25 percent of the polymer that has a plurality of polymerizable vinyl groups, about 25 to about 85 percent of the fluoroaluminosilicate glass, about 0.2 to about 5 percent of the combined weight of the redox cure system and about 1 to about 30 percent of the combined weight of water and any added solvents, diluents or $\alpha,\beta$-unsaturated monomers.

11. A cement according to claim 1, comprising by weight about 1 to about 10 percent of the polymer that is substantially free of polymerizable vinyl groups, about 5 to about 20 percent of the polymer that has a plurality of polymerizable vinyl groups, about 45 to about 75 percent of the fluoroaluminosilicate glass, about 0.5 to about 5 percent of the combined weight of the redox cure system and about 5 to about 20 percent of the combined weight of water and any added solvents, diluents or $\alpha,\beta$-unsaturated monomers.

12. A cement according to claim 1, further comprising a photoinitiator.

13. A glass ionomer cement kit comprising two or more containers whose contents collectively comprise:
   a) polymer having a plurality of acidic repeating units but being substantially free of polymerizable vinyl groups;
   b) polymer having a plurality of acidic repeating units and a plurality of polymerizable vinyl groups;
   c) fluoroaluminosilicate glass;
   d) redox cure system that can initiate dark cure of the vinyl groups; and
   e) water;
together with instructions for use of the cement kit.

14. A kit according to claim 13, further comprising one or more auxiliary devices that help a user to prepare and use the cement.

15. A kit according to claim 13, comprising an anhydrous mixture of fluoroaluminosilicate glass and the polymer that is substantially free of polymerizable vinyl groups in a first container, and water in a second container.

16. A kit according to claim 13, comprising an anhydrous mixture of fluoroaluminosilicate glass and the polymer having a plurality of polymerizable vinyl groups in a first container, and water in a second container.

17. A kit according to claim 13, comprising a paste containing fluoroaluminosilicate glass in a first container and a liquid containing water in a second container.

18. A kit according to claim 13, comprising a paste containing fluoroaluminosilicate glass in a first container and a paste containing non-acid-reactive filler in a second container.

19. A kit according to claim 13, comprising by weight about 0.5 to about 30 percent of the polymer that is substantially free of polymerizable vinyl groups, about 1 to about 30 percent of the polymer that has a plurality of polymerizable vinyl groups, less than about 90 percent of the fluoroaluminosilicate glass, about 0.01 to about 10 percent of the combined weight of the redox cure system and about 0.5 to about 40 percent of the combined weight of water and any added solvents, diluents or $\alpha,\beta$-unsaturated monomers.

20. A method for making a glass ionomer cement comprising mixing cement components comprising:
   a) polymer having a plurality of acidic repeating units but being substantially free of polymerizable vinyl groups;
   b) polymer having a plurality of acidic repeating units and a plurality of polymerizable vinyl groups;
   c) fluoroaluminosilicate glass;
   d) redox cure system that can initiate dark cure of the vinyl groups; and
   e) water;
and allowing the resulting mixture to cure.

21. A method according to claim 20, wherein the surface of the fluoroaluminosilicate glass is treated with acid, phosphate, chelating agent, silane or silanol prior to mixing.

22. A method according to claim 20, wherein the fluoroaluminosilicate glass is treated with a solution of a treatment agent and the pH of the solution or the treated glass is adjusted to neutral or near-neutral, thereby increasing storage stability of the cement components.

23. A method according to claim 20, wherein at least one component of the redox cure system is encapsulated prior to mixing.

24. A method according to claim 20, wherein the cement components are provided as a multi-part product comprising fluoroaluminosilicate glass and the polymer that is substantially free of polymerizable vinyl groups in a first anhydrous part, and water in a second part.

25. A method according to claim 20, wherein the cement components are provided as a multi-part product comprising fluoroaluminosilicate glass and the polymer having a plurality of polymerizable vinyl groups in a first anhydrous part, and water in a second part.

26. A method according to claim 20, wherein the cement components are provided as a multi-part product at least one part of which is lyophilized or otherwise dried.

27. A method according to claim 20, wherein the cement components are provided as a paste/liquid product that comprises fluoroaluminosilicate glass in the paste and water in the liquid.

28. A method according to claim 20, wherein the cement components are provided as a paste/paste product that comprises fluoroaluminosilicate glass in a first paste and a non-acid-reactive filler in a second paste.

29. A method according to claim 20, wherein the cement components are provided as a preformed article.

30. A method according to claim 20, wherein the cement components comprise by weight about 0.5 to about 30 percent of the polymer that is substantially free of polymerizable vinyl groups, about 1 to about 30 percent of the polymer that has a plurality of polymerizable vinyl groups, less than about 90 percent of the fluoroaluminosilicate glass, about 0.01 to about 10 percent of the combined weight of the redox cure system and about 0.5 to about 40 percent of the combined weight of water and any added solvents, diluents or $\alpha,\beta$-unsaturated monomers.

31. A method according to claim 20, wherein the cement components comprise by weight about 0.5 to about 20 percent of the polymer that is substantially free of polymerizable vinyl groups, about 1 to about 25 percent of the polymer that has a plurality of polymerizable vinyl groups, about 25 to about 85 percent of the fluoroaluminosilicate glass, about 0.2 to about 5 percent of the combined weight of the redox cure system and about 1 to about 30 percent of the combined weight of water and any added solvents, diluents or $\alpha,\beta$-unsaturated monomers.

32. A method according to claim 20, wherein the cement components comprise by weight about 1 to about 10 percent of the polymer that is substantially free of polymerizable vinyl groups, about 5 to about 20 percent of the polymer that has a plurality of polymerizable vinyl groups, about 45 to about 75 percent of the fluoroaluminosilicate glass, about 0.5 to about 5 percent of the combined weight of the redox cure system and about 5 to about 20 percent of the combined weight of water and any added solvents, diluents or $\alpha,\beta$-unsaturated monomers.

33. A method according to claim 20, where the cure takes place in the dark.

34. A method according to claim 20, wherein the cement components further comprise a photoinitiator.

35. A method for treating tooth tissue, comprising:
   a) mixing a:
      i. polymer having a plurality of acidic repeating units but being substantially free of polymerizable vinyl groups;
      ii. polymer having a plurality of acidic repeating units and a plurality of polymerizable vinyl groups;
      iii. fluoroaluminosilicate glass;
      iv. redox cure system that can initiate dark cure of the vinyl groups; and
      v. water;
   b) placing the resulting mixture in contact with the tooth tissue; and
   c) allowing the mixture to cure.

36. A method according to claim 35, wherein the resulting mixture comprises by weight about 0.5 to about 30 percent of the polymer that is substantially free of polymerizable vinyl groups, about 1 to about 30 percent of the polymer that has a plurality of polymerizable vinyl groups, less than about 90 percent of the fluoroaluminosilicate glass, about 0.01 to about 10 percent of the combined weight of the redox cure system and about 0.5 to about 40 percent of the combined weight of water and any added solvents, diluents or $\alpha,\beta$-unsaturated monomers.

37. A method according to claim 35, wherein the cure takes place in the dark.

38. A method according to claim 35, wherein the resulting mixture is placed using an atraumatic or a minimal intervention restorative technique.

39. A method according to claim 35, wherein the resulting mixture is placed without using a tooth pretreatment.

40. A method according to claim 35, wherein the resulting mixture is used to attach an orthodontic device to the tooth tissue.

* * * * *